US006620620B1

United States Patent
Anderson et al.

(10) Patent No.: US 6,620,620 B1
(45) Date of Patent: Sep. 16, 2003

(54) MICRO LIQUID EVAPORATOR

(75) Inventors: John Lynde Anderson, Chattanooga, TN (US); Ross F. Russell, Chattanooga, TN (US); David O. Hanon, Ringgold, GA (US); James Nelson Edwards, Chattanooga, TN (US)

(73) Assignee: ERA Systems, Inc., Chattanooga, TN (US)

( * ) Notice: Subject to any disclaimer, the term of this patent is extended or adjusted under 35 U.S.C. 154(b) by 270 days.

(21) Appl. No.: 09/718,645

(22) Filed: Nov. 22, 2000

Related U.S. Application Data (63) Continuation-in-part of application No. 09/066,993, filed on Apr. 27, 1998, now abandoned.

(51) Int. Cl.[7] .......................... B01L 3/02; G01N 21/29; G01N 35/08; G01N 1/10; G01N 35/00; G05D 9/00; G05D 7/00; B01D 1/00
(52) U.S. Cl. .......................... 436/55; 436/180; 436/54; 436/46; 422/100; 422/82.05; 422/106; 422/110; 159/44; 73/863.32; 73/864; 73/864.01; 73/864.11; 73/864.16; 73/864.24; 73/864.25; 73/864.31
(58) Field of Search .......................... 422/82.05, 100, 422/106, 110; 73/863.32, 864, 864.01, 864.11, 864.13, 864.16, 864.24, 864.25, 864.31; 159/44; 436/180, 55, 54, 46

(56) References Cited

U.S. PATENT DOCUMENTS 4,041,995 A * 8/1977 Columbus .................. 141/275
4,436,428 A    3/1984 Watanabe et al.
4,552,723 A    11/1985 Adams et al.
4,794,086 A    12/1988 Kasper et al.
4,814,612 A    3/1989 Vestal et al.
4,823,009 A    4/1989 Biemann et al.

(List continued on next page.)

Primary Examiner—Jill Warden
Assistant Examiner—B. R Gordon
(74) Attorney, Agent, or Firm—Chambliss, Bahner & Stophel, P.C.

(57) ABSTRACT

The drop-by-drop evaporation of a liquid or solution is controlled by monitoring the disappearance of each successive droplet and by actuating the deposition of the next droplet until the desired volume is deposited. In the case of a solution, non-volatile residue (NVR) is collected on a deposition surface plate as a relatively small mound. One of a variety of methods may be employed to measure the evaporative behavior of each droplet and to key the deposition procedure. The process is preferably carried out employing a clean deposition surface plate that is maintained at or below the boiling point of the particular liquid or solvent being deposited. The environment is preferably controlled so that inadvertent contamination is precluded from interfering, and thus the method permits the automatic, micro-processor controlled evaporation of liquids with the resultant deposition of non-volatile residues from solutions within relatively short periods of time. The deposited residue may then be quantified at levels down to and below about 1 ug/mL (1 mg/L) by one of several means for determining the amount of non-volatile residue remaining.

20 Claims, 8 Drawing Sheets

U.S. PATENT DOCUMENTS

| | | | |
|---|---|---|---|
| 4,908,512 A | 3/1990 | Caprioli et al. | |
| 5,074,658 A | 12/1991 | Tavlarides et al. | |
| 5,098,657 A | 3/1992 | Blackford et al. | |
| 5,298,967 A | 3/1994 | Wells et al. | |
| 5,374,396 A | 12/1994 | Blackford et al. | |
| 5,441,878 A | 8/1995 | Thies et al. | |
| 5,494,829 A * | 2/1996 | Sandstrom et al. | 436/518 |
| 5,528,923 A | 6/1996 | Ledez et al. | |
| 5,560,889 A | 10/1996 | Ogino | |
| 5,679,580 A | 10/1997 | Ball et al. | |
| 5,698,774 A | 12/1997 | Osmanski | |
| 5,707,588 A * | 1/1998 | Tsukishima | 422/99 |
| 5,762,877 A * | 6/1998 | Brewer | 422/100 |
| 5,774,033 A | 6/1998 | Antonelli | |
| 5,879,627 A * | 3/1999 | Tanihata | 422/67 |
| 5,958,345 A * | 9/1999 | Turner et al. | 422/104 |
| 6,086,722 A * | 7/2000 | Webster et al. | 203/12 |
| 6,296,809 B1 * | 10/2001 | Richards et al. | 422/64 |
| 6,309,508 B1 * | 10/2001 | Lemme et al. | 159/49 |
| 6,352,861 B1 * | 3/2002 | Copeland et al. | 436/46 |
| 6,372,185 B1 * | 4/2002 | Shumate et al. | 422/100 |
| 6,387,330 B1 * | 5/2002 | Bova et al. | 422/100 |
| 6,416,713 B1 * | 7/2002 | Ford et al. | 422/63 |

* cited by examiner

MICRO LIQUID EVAPORATOR

CROSS REFERENCE TO RELATED APPLICATIONS

This application is a continuation-in-part of the copending application entitled "Micro Solvent Evaporator," which was filed on Apr. 27, 1998 and assigned a Ser. No. of 09/066,993, the disclosure of which is fully incorporated herein by reference.

FIELD OF INVENTION

This invention generally relates to an apparatus and method for the controlled evaporation of liquids, including solutions. More particularly, the preferred embodiment of this invention comprises an improved apparatus and method for evaporating the solvent of a solution on a drop-by-drop basis. A preferred embodiment of the invention also provides means for measuring the amount of the solute remaining after the solvent has substantially evaporated.

BACKGROUND AND DESCRIPTION OF THE PRIOR ART

It is known that the amount of solute contained in a quantity of solution may be measured by a variety of means after the solvent of the solution has evaporated. Current methods for the deposition and measurement of solvent non-volatile residue (NVR), however, suffer from a variety of problems.

The most common method involves removing the solvent and thereby concentrating the residue by atmospheric evaporation of 100 to 1000 mL of liquid solvent followed by weighing the residue. This method has many inherent errors and problems that may result in substantial errors in measurement, particularly at concentration levels (solute/solvent) of less than 3 mg/L or its equivalent. One additional problem associated with boiloff evaporation and release of the vapor to the atmosphere is that the process may be hazardous to the environment and to laboratory workers. Even when the solvent is partially removed by in vacuo distillation, the final 20–25 mL are routinely released to the environment by thermal evaporation. A variety of ASTM methods specify the evaporative removal of solvents followed by weighing of residues, such as ASTM F331, E1235M, and E1731M.

Other more recent methods of evaporating solvents and/or of measuring non-volatile residue in solvents are described in U.S. Pat. Nos. 5,679,580; 5,560,889; 5,374,396; and 5,698,774.

It would be desirable if the evaporation of a liquid, such as a solution, could be controlled on a drop-by-drop basis. It would be further desirable if the measurement of solvent non-volatile residue could be performed accurately, particularly at concentrations of less than 3 mg/L or its equivalent. Finally, it would be desirable if the controlled evaporation of a solution and the accurate measurement of the NVR did not result in any significant release of hazardous material.

ADVANTAGES OF THE INVENTION

Among the advantages of the invention is the controlled evaporation of a liquid, such as a solution, on a drop-by-drop basis. Another advantage of the invention is the accurate measurement of NVR, particularly at concentrations of less than 3 mg/L. A further advantage of the invention is the reduction in the amount of hazardous material released into the environment as a result of the evaporation of the liquid or solvent.

Additional objects and advantages of this invention will become apparent from an examination of the drawings and the ensuing description.

EXPLANATION OF TECHNICAL TERMS

As used herein, the term solvent non-volatile residue or NVR refers to any substance contained in a solution, which substance is substantially not susceptible to evaporation at common temperatures and pressures and which substance remains after evaporation of the solvent of the solution.

As used herein, the term inert gas refers to a gas or mixture of gases which are generally unreactive and lacking active chemical or physiological properties, which may include, but are not limited to the inert gases of Group 0 of the periodic table of elements as well as other similar gases, elements, compounds and mixtures that exist in the gaseous state at common atmospheric pressures and temperatures. Nitrogen is the preferred inert gas for use in connection with this invention, but others may be used.

As used herein, the term droplet refers to a small amount of liquid or solution that falls separately from a depositing device, such as a syringe, and adheres to a deposition surface plate in a generally round-shaped globule.

As used herein, the term ultra-clean refers to a condition exceeding that of common laboratory conditions in terms of the elimination of foreign matter and contamination from the environment.

SUMMARY OF THE INVENTION

The present invention provides an automatic, controlled method and apparatus for the evaporation of a volume of a liquid, such as a solution (including a volume of less than about 5 mL). Where the liquid is a solution containing non-volatile residue ("NVR"), the invention provides for deposition of NVR into a small controlled area on a suitable clean deposition surface plate for subsequent measurement by one of several available methods. Preferably, the deposition surface plate is essentially flat or concave.

More particularly, this invention provides a feedback-controlled automated method for the deposition of a volume of liquid, such as a solution, using a controlled motor or other suitable device to intermittently push down or actuate a depositing device, such as a syringe plunger, in order to deposit a successive series of small droplets onto a deposition surface plate. The actuation of the depositing device is controlled in response to a determination that at least a portion of the liquid in a droplet on the deposition surface plate has evaporated. In other words, the evaporative disappearance of each successive droplet is monitored so that the next droplet is deposited only when the preceding droplet has at least partially evaporated. This process automatically continues until the desired amount of liquid has substantially evaporated and, in the case where the liquid is a solution containing NVR, the non-volatile residue has been accumulated on the deposition surface plate.

A deposition needle with a very small internal diameter (e.g. less than about 0.5 mm) and preferably having a flat or blunt open end is employed as part of the depositing device so that capillary forces act to prevent inadvertent deposition of droplets. The temperature of the deposition surface may be measured and controlled to increase the evaporation rate of higher boiling point liquids or solvents. A flow of a purge gas, generally gaseous nitrogen or another inert gas, is preferably employed to sweep across the deposition surface plate in a circular pattern (or other pattern generally flowing around or across the deposition surface plate), to aid in the proper evaporative conditions, to prevent any possible vapor/oxygen explosive conditions, and to maintain the deposition surface plate and the deposited residue in an environmentally clean condition.

A variety of liquid or solvent droplet detection methods may be used to trigger the deposition process so that the desired volume will be deposited in sequential droplets automatically. One preferred method is the appearance of increased light to a suitable light sensitive detector as the result of the evaporation of at least a portion of the droplet. Another such method involves the change in spectral distribution of reflected light as at least a portion of the liquid or solvent in the droplet evaporates, which change is detected photo-electrically. Yet another method involves the measurement of the decreasing concentration of already evaporated liquid or solvent vapor in the purge gas as at least a portion of the liquid or solvent evaporates. Still another method involves monitoring the change in the weight on the deposition surface plate caused by the evaporation of at least a portion of the liquid or solvent that is deposited thereon. Another method of merit involves the use of piezo-electric sensing of the evaporation of at least a portion of each successive droplet.

Yet another method is the detection of light from a suitable light source using a video camera that is focused on a portion of the deposited droplet in such a way that the presence of the droplet obscures the light from the source. This physical obscuring of the light from the source disappears as at least a portion of the droplet evaporates. The wetting of the liquid or solvent to the needle and the deposition surface plate can be used to advantage in controlling in part the physical shape of the droplet.

Following completion of the successive depositions, the amount of NVR remaining can readily be determined quantitatively by a variety of methods down to and below about 1 microgram per milliliter (which is equivalent to about 1 mg per liter or, for a solvent density of 1, about one part per million or PPM). Thus, for example, the method detailed in U.S. Pat. No. 3,297,874 and subsequent continuations-in-part (all now expired) permits the quantitative measurement of residue in amounts as low as 1 nanogram on an ultra-clean deposition surface.

Another method for measuring residues quantitatively and qualitatively in amounts less than about 1 microgram involves the use of very low grazing angle FTIR technology. Yet another method for determining the presence of residues in such amounts is through use of a quartz crystal micro-balance in which a clean quartz crystal is used as the deposition surface. Other methods known to those having ordinary skill in the art to which the invention relates may also be used. In all cases, calibration of the overall method may be carried out simply by evaporating solvents with known amounts of residues and determining the appropriate relationships of the amount of deposited residues to the measurement responses.

The invention may be employed to evaporate solvents such as those primarily of an organic nature, such as hexanes and other hydrocarbons, halogenated hydrocarbons, CFC-113 and replacements for CFC-113, other halogenated solvents, alcohols, ketones, esters, organic acids, and the like, although aqueous solvents may also be evaporated according to the invention. In addition, liquids and solvents boiling below about 130° Celsius may be evaporated according to the invention at 1 atmosphere, whereas higher boiling point liquids and solvents may be evaporated according to the invention in vacuo.

DESCRIPTION OF THE PREFERRED EMBODIMENTS OF THE INVENTION

Figure 1:
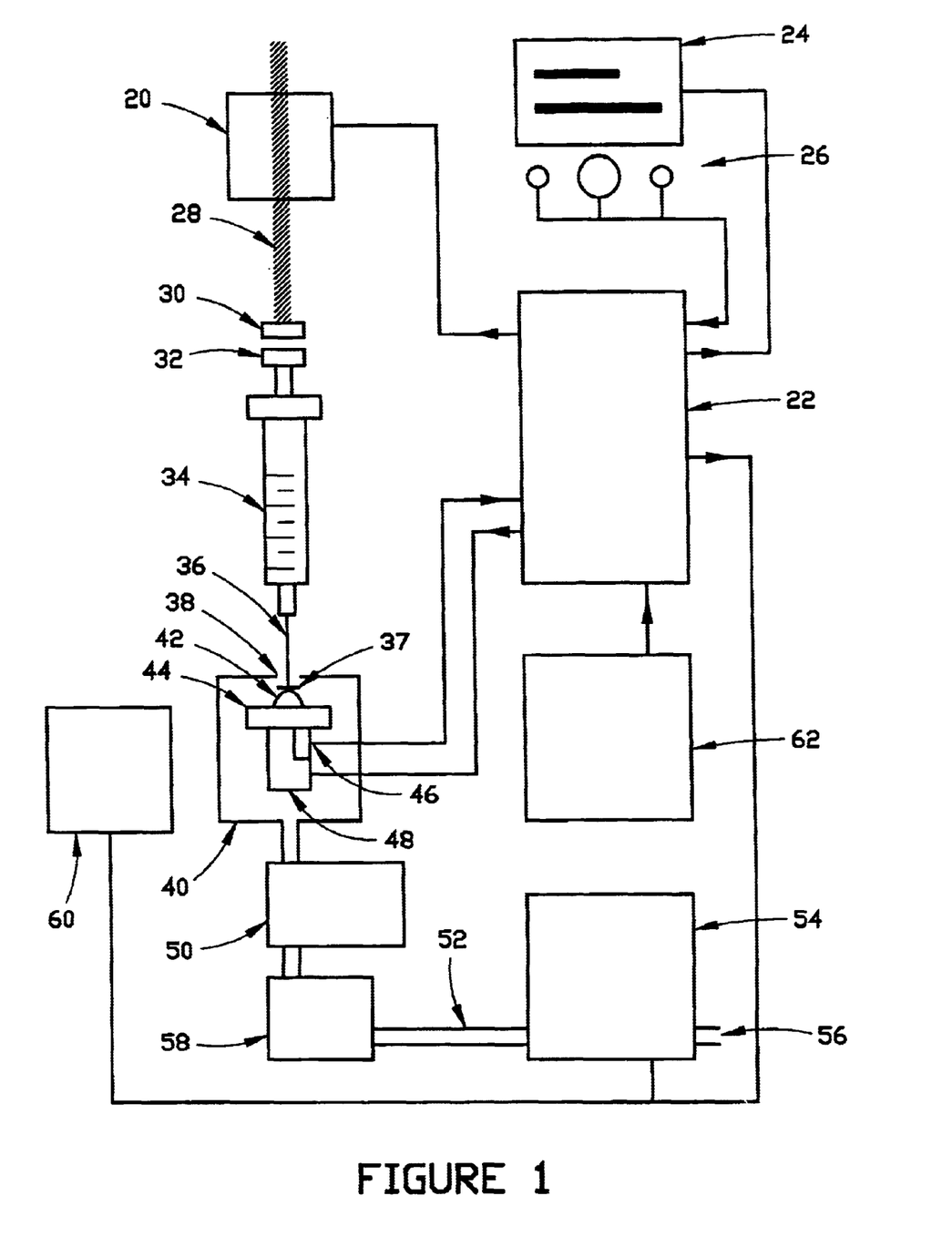
FIG. 1 is a block and functional diagram showing deposition and droplet detection apparatus with operator display and control components.
Figure 8:
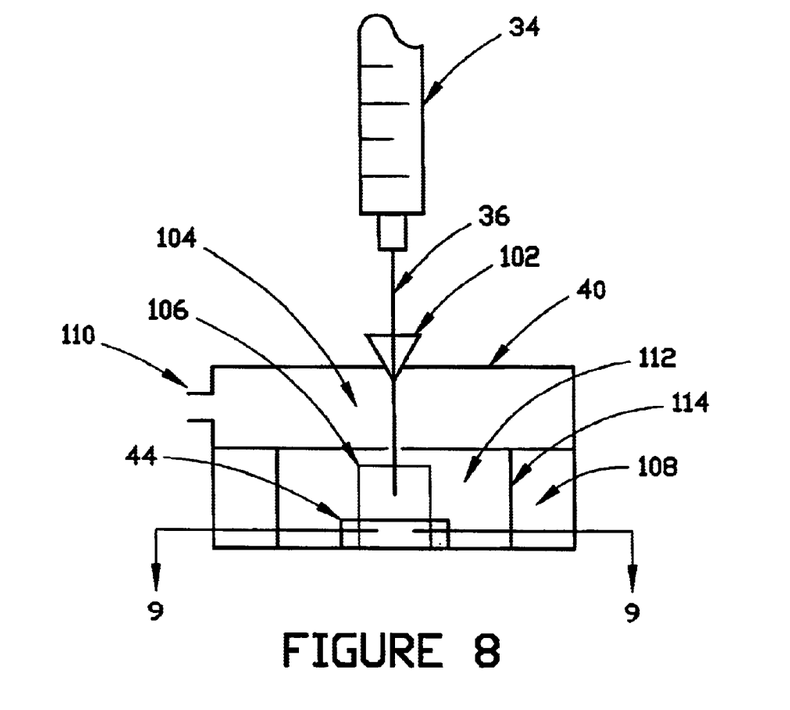
FIG. 8 is a detailed side view representation of the enclosure employed for directing the preferred circular purge gas flow about the deposition surface.
Figure 9:
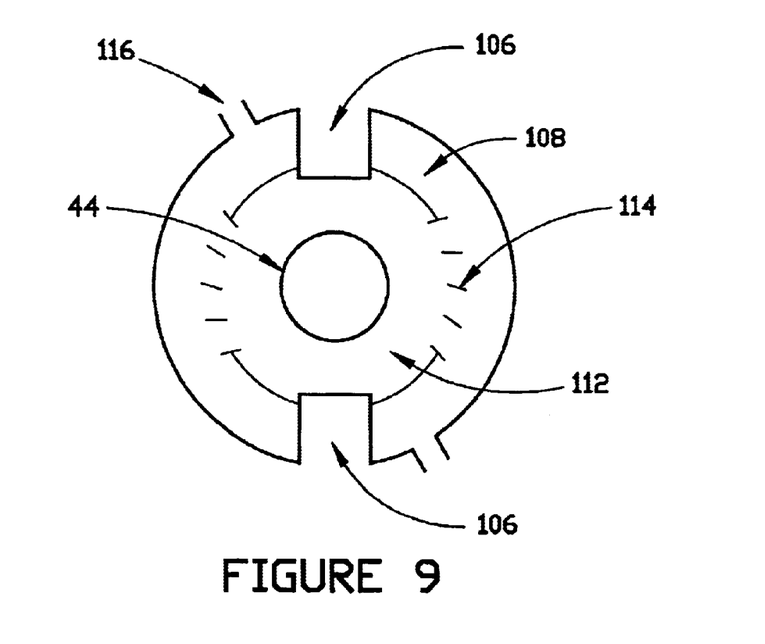
FIG. 9 is a detailed sectional view of the enclosure of FIG. 8, taken through line 9—9.

The overall design of the micro-liquid evaporator is shown in FIG. 1 with block representations of certain components, the nature of which would be known to those having ordinary skill in the art to which the invention relates. Six of the preferred liquid or solvent-loss detection means are shown in FIGS. 2 through 7. Obviously, the means of detecting the evaporation of the liquid or solvent droplet may be any practical method, as shown or other than those shown, that performs the process of measuring the loss of liquid or solvent during the evaporative process. Two views of a testing enclosure are shown in FIGS. 8 and 9. Other enclosure arrangements providing similar effects may also be used. The inventions hereinafter described and claimed are the unique combinations of the several parts of the apparatus that permit the automated, controlled evaporative process to occur.

The overall detail and logical arrangements of a preferred embodiment of the invention are illustrated in FIG. 1. A stepping motor 20 or other equivalent device receives power from the power, logic and computing section 22 to rotate spiral shaft 28 of the stepping motor or other equivalent device so as to actuate a depositing device, such as a syringe. Shaft 28 moves non-rotating end section 30 vertically downwardly in order to depress syringe plunger 32 within syringe body 34 which contains the liquid or solution being deposited. A needle 36 with a minimal bore of less than about 0.5 mm and preferably less than about 0.3 mm I.D. extends from the syringe through top access hole 38 of enclosure 40, and is sealed with a seal, such as conical device 102, which is illustrated FIG. 8. Droplet 42 is shown prior to appreciable evaporation, and in contact with needle 36 and deposition surface plate 44. In a preferred embodiment, collar 37 is provided around the exterior of needle 36 above droplet 42 to inhibit the tendency of the droplet to creep up the needle. Temperature sensor 46 measures the temperature of the deposition surface plate 44. The temperature of heater 48, which is in contact with deposition surface plate 44, is maintained by the power, logic and computing section and selected by the operator using the display module 24 and the appropriate controls 26. Enclosure 40, shown in more detail in FIGS. 8 and 9, directs the purge gas or, more specifically, the gaseous nitrogen or other inert gas about the evaporating droplet so as to increase and standardize the evaporative process, to maintain a clean condition during the evaporative process, and to prevent inadvertent contamination from the areas outside the enclosure. Purge gas heater 50, located in passageway 52, heats the purge gas in cooperation with pressure regulator 54, inlet 56 and filter 58. FIGS. 2–7 illustrate various embodiments of detection transmitter 60 and droplet detection receiver 62, which measure the level of evaporation of droplet 42, but the invention is not limited to those embodiments.

Figure 2A:
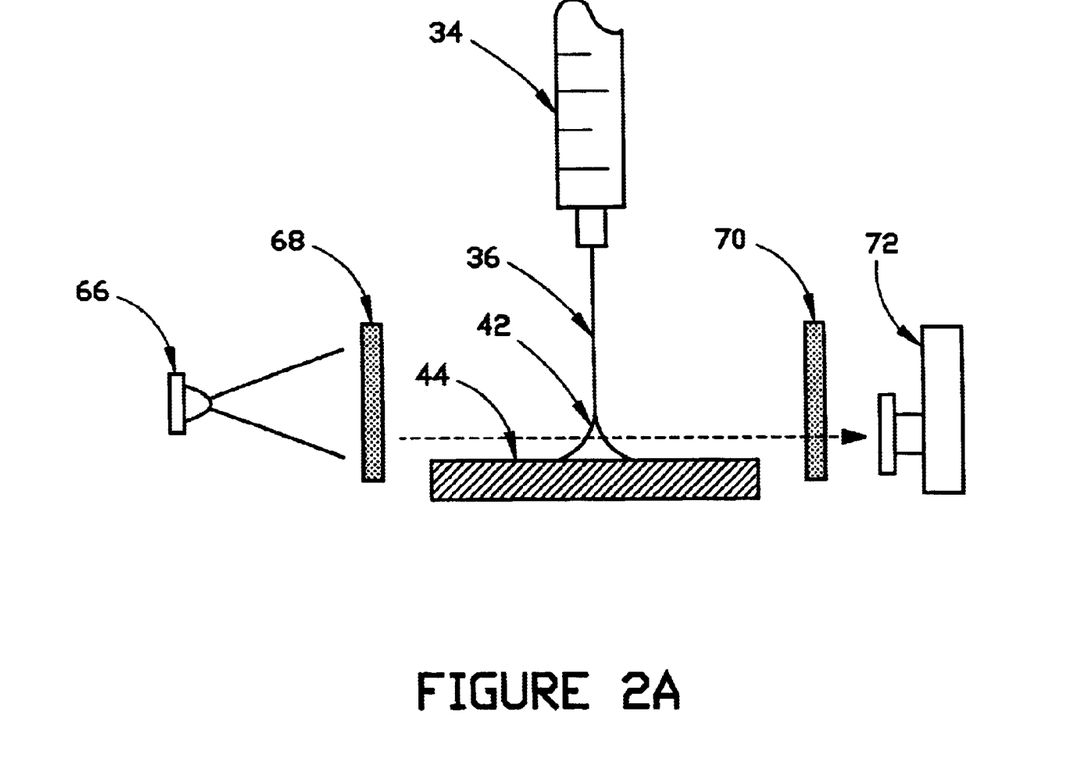
FIG. 2A is a detailed representation of the use of a video camera and light source apparatus for detecting droplet evaporation.
Figure 2B:
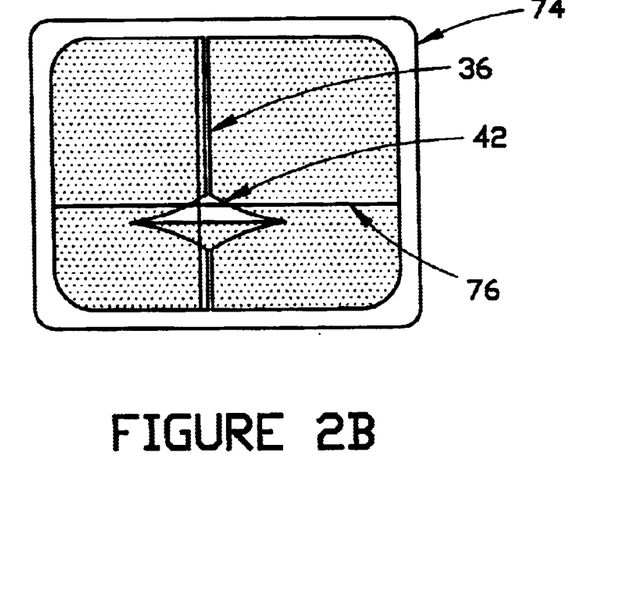
FIG. 2B is an illustration of the video camera monitor screen display, including artificial crosshairs which are used to measure droplet evaporation.

FIGS. 2A and 2B illustrate the arrangements used in the droplet sensing method known as video drop sensing. Droplet 42 is deposited from needle 36 of syringe 34 onto deposition surface plate 44. Light source 66 directs light through light diffuser 68, droplet 42 and optional diffuser 70 to video camera 72. As shown in FIG. 2B, video screen 74 (which may be a component of display 24) includes crosshairs 76 which are movable by controls 26 so as to permit the operator to determine a change in the light obscuration as the droplet evaporates. Video camera 72 is interfaced with the power, logic and computing module 22 shown in FIG. 1 so that a change in light obscuration due to the evaporation of at least a portion of the liquid or solvent permits the next successive droplet to be deposited in a timely manner. In a preferred embodiment, a blue or other colored filter may be used to improve the sensitivity of the video camera, and a blunt end needle may be used to improve the wetting of the droplet to the needle.

Figure 3:
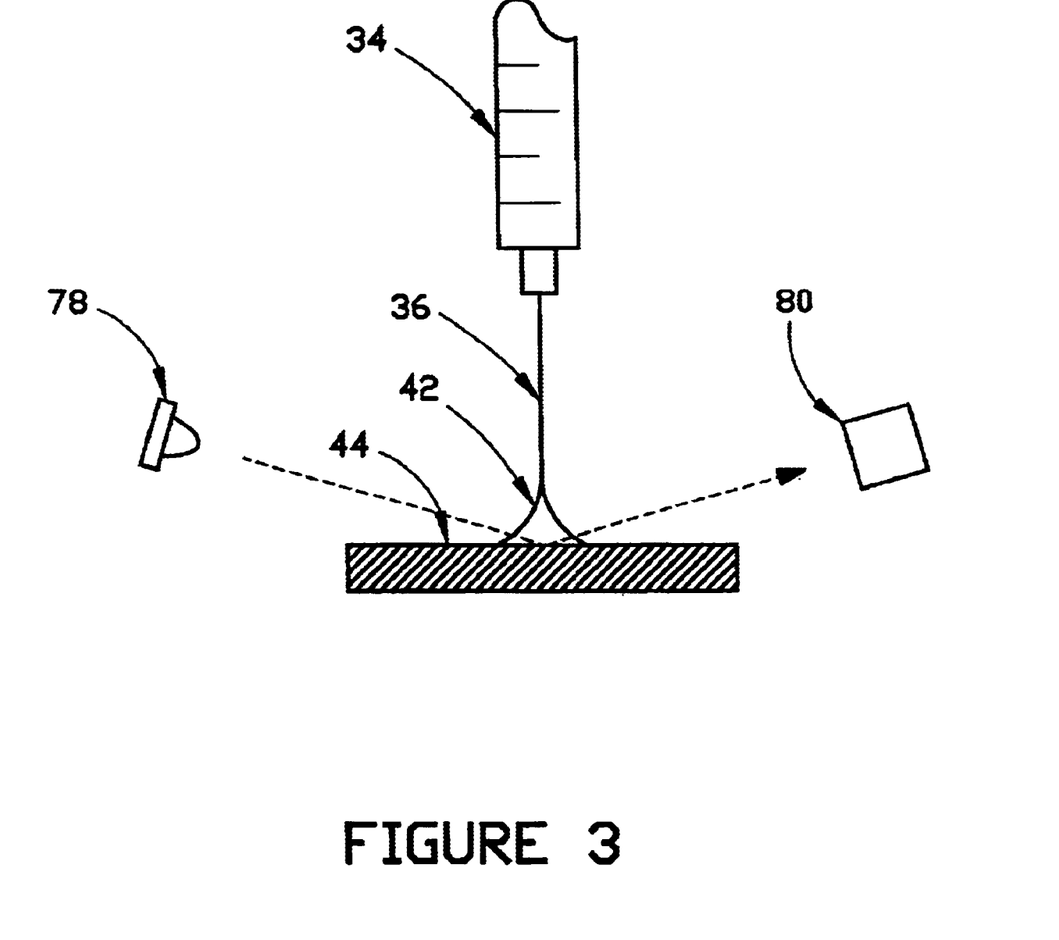
FIG. 3 is a detailed representation of the use of a reflected laser beam to detect the disappearance of the solvent droplet by monitoring the change in the spectral distribution of the reflected beam.

FIG. 3 is a visual representation of the sensing of the evaporative process by means of the change in a reflected laser beam. Droplet 42 is deposited from needle 36 of syringe 34 onto deposition surface plate 44. Laser 78 directs a laser beam at the droplet on deposition surface plate 44, which beam is reflected toward detector 80. When the liquid or solvent droplet has not yet fully evaporated, the reflected beam is scattered and the detector 80 does not yet receive the full beam. Detector 80 is interfaced with the power, logic, and computing module 22 shown in FIG. 1 so that a change in the spectral distribution of the reflected laser beam due to the evaporation of at least a portion of the liquid or solvent permits the next successive droplet to be deposited in a timely manner.

Figure 4:
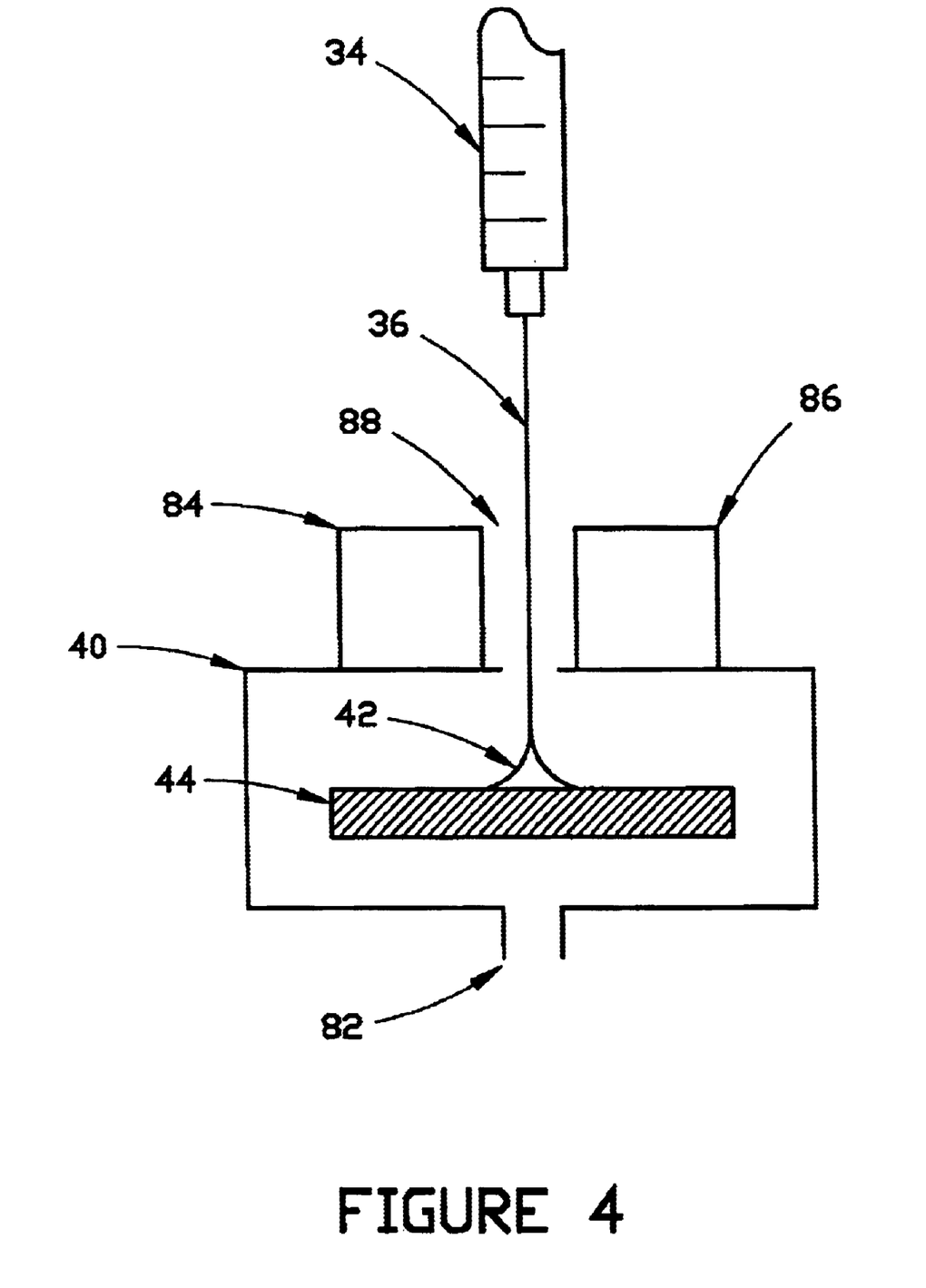
FIG. 4 is a detailed representation of the use of a vapor detector to monitor the evaporation process.

FIG. 4 is a visual representation of the method of detecting the evaporative process based on monitoring the off-gases containing the liquid or solvent vapors. Droplet 42 is deposited from needle 36 of syringe 34 onto deposition surface plate 44. Purge gas is introduced into enclosure 40 through purge gas inlet 82. Detectors 84 and 86 measure the concentration of the off-gas vapors passing through passageway 88 as the droplet evaporates. Detectors 84 and 86 are interfaced with the power, logic, and computing module 22 shown in FIG. 1 so that a change in off-gas concentration due to the evaporation of at least a portion of the liquid or solvent permits the next successive droplet to be deposited in a timely manner. It should be noted that the relative positions of purge gas inlet 82 and passageway 88 are representations only and are not to be construed as being the required positions with respect to the evaporative process as is shown in FIGS. 8 and 9.

Figure 5:
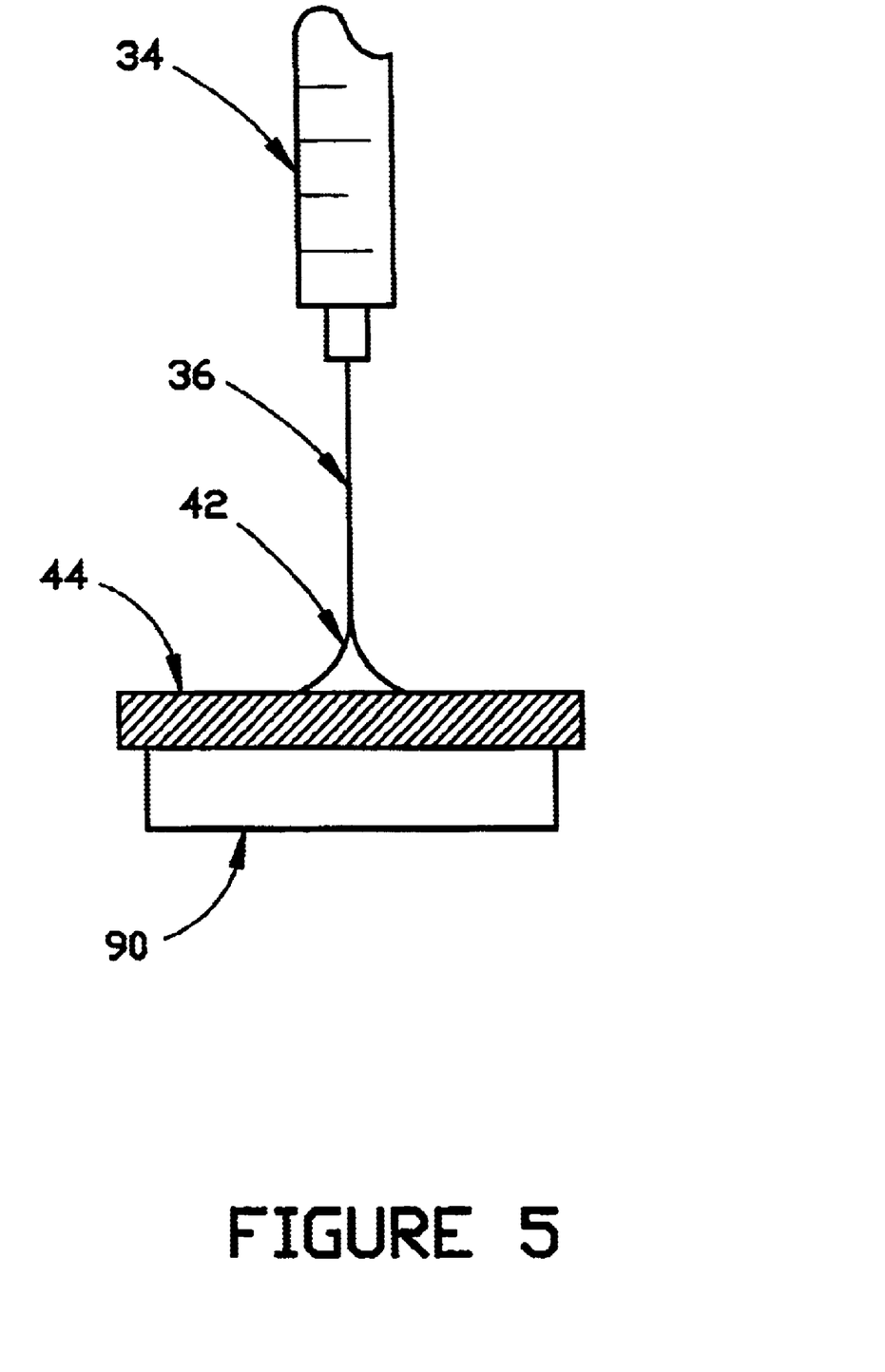
FIG. 5 is a detailed representation of the use of measuring the decreasing weight of the evaporating solvent by means of a weigh cell to monitor the evaporation process.

FIG. 5 is a visual representation of weight drop sensing as a method for sensing droplet evaporation. Droplet 42 is deposited from needle 36 of syringe 34 onto deposition surface plate 44. Weigh cell 90 is interfaced with the power, logic, and computing module 22 shown in FIG. 1 so that a reduction in weight due to the evaporation of at least a portion of the liquid or solvent permits the next successive droplet to be deposited in a timely manner.

Figure 6:
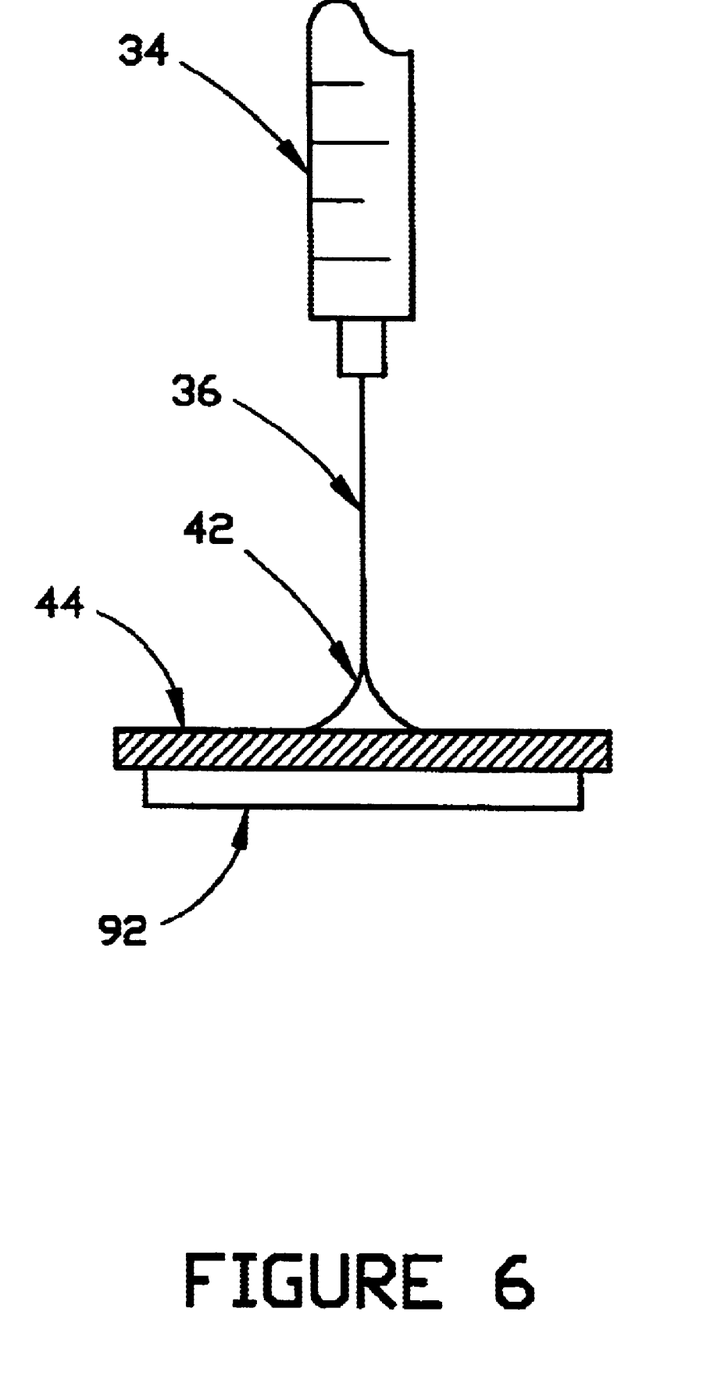
FIG. 6 is a detailed representation of the use of a piezo-electric crystal to sense the disappearance of the solvent droplet and thereby monitor the evaporation process.

FIG. 6 illustrates the use of deflections of a piezo-electric crystal 92 as a means for detecting the evaporation of liquid or solvent from a droplet. Droplet 42 is deposited from needle 36 of syringe 34 onto deposition surface plate 44. Piezo-electric crystal is interfaced with the power, logic and computing module 22 shown in FIG. 1 so that a change in the deflections of the piezo-electric crystal due to the evaporation of at least a portion of the liquid or solvent permits the next successive droplet to be deposited in a timely manner.

Figure 7:
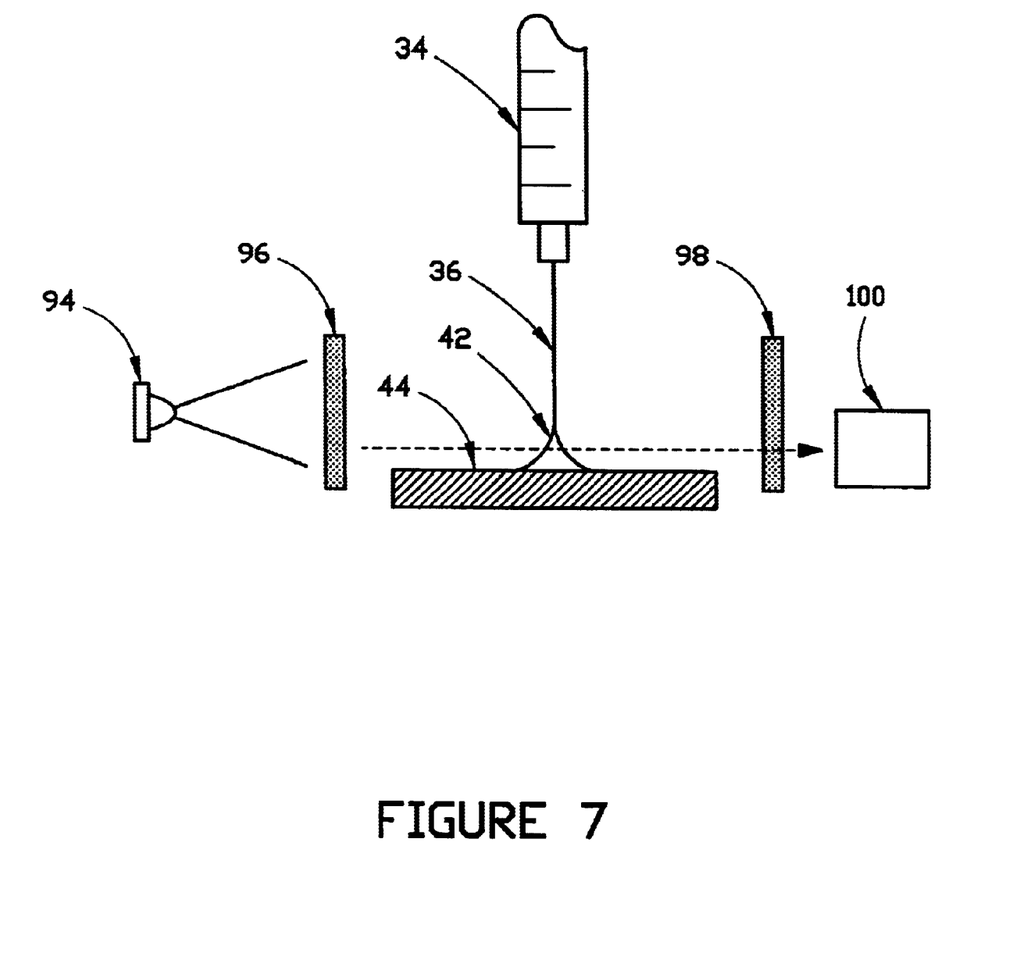
FIG. 7 is a detailed representation of the use of a light sensitive detector to monitor the disappearance of the evaporating solvent droplet.

FIG. 7 is a representation of a more general evaporation detector by photo-electric sensing somewhat similar to FIG. 2. Droplet 42 is deposited from needle 36 of syringe 34 onto deposition surface plate 44. Light source 94 directs light through diffuser 96, droplet 42 and optional filter 98 to detector 100. Detector 100 is interfaced with the power, logic and computing module 22 shown in FIG. 1 so that a change in light intensity due to the evaporation of at least a portion of the liquid or solvent permits the next successive droplet to be deposited in a timely manner.

FIG. 8 is a side view representation of a preferred embodiment of enclosure 40 shown in FIG. 1, which controls the inside environment during droplet evaporation, creates a generally circular pattern of purge gas flow about the evaporating droplet, and prevents inadvertent contamination. A droplet is deposited from needle 36 of syringe 34 through conical seal 102, which closes an access hole on the top of enclosure 40 and maintains the needle generally centered in the top access hole. The droplet is deposited onto deposition surface plate 44. Enclosure 40 includes two windows 106, one of which permits a light or laser beam to enter while the other permits a sensor to detect changes in the light pattern as the droplet evaporates. Purge gas enters the enclosure through one of the two purge gas entry plenums 108, and exits the enclosure through exit plenum 104 and purge gas exit 110. The purge gas moves in a generally circular pattern within the central evaporation area 112 of the enclosure; purge gas deflectors 114 may be used to enhance the generally circular pattern of the purge gas around the droplet.

FIG. 9 is a sectional view of enclosure 40 at line 9—9 of FIG. 8. Purge gas enters the enclosure through purge gas entrances 116, which are depicted on opposite sides of enclosure 40 (i.e., 180 degrees from each other). Deflectors 114 move the purge gas in a generally circular pattern around plenum 108. 44 is the deposition surface plate, 112 is the central evaporation area, and 106 represents the two windows also shown in FIG. 8. While FIGS. 8 and 9 depict enclosure 40 as circular in shape, it is understood that enclosure 40 may be any other suitable shape.

The use of the video monitor as a means of detecting the evaporation of the liquid or solvent droplet has the additional advantage of permitting the visual confirmation of the evaporative process even inside a closed purge gas enclosure. This is an advantage not generally available in the other means cited.

The invention can be hardwired or, preferably, use a preprogrammed microprocessor to control the overall goals of the automatic, controlled evaporation of a liquid or a solvent and the deposition of non-volatile residue onto a deposition surface plate, which may thereafter be measured by other means. Three of those other means are described herein. In addition, the power, logic and computing module 22 may be adapted to store a plurality of physical data relating to a variety of different liquids and solutions, which may be entered by means of controls 26, to permit the apparatus to be operated at pre-set calibrations which are known to be effective and useful with such various different liquids and solutions.

Although this description contains many specifics, these should not be construed as limiting the scope of the invention, but merely as providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. An apparatus for effecting the controlled evaporation of a liquid, said apparatus comprising:
   (a) a deposition surface plate;
   (b) a device for depositing a droplet of the liquid onto the deposition surface plate;
   (c) means for detecting the evaporation of at least a portion of the droplet of the liquid on the deposition surface plate;
   (d) means for intermittently actuating the device for depositing a droplet of the liquid onto the deposition surface plate;
   (e) means for controlling the device for depositing a droplet of the liquid onto the deposition surface plate in response to a determination that at least a portion of the liquid on the deposition surface plate has evaporated.

2. The apparatus of claim 1 which includes means for controlling the device for depositing a droplet of the liquid onto the deposition surface plate in response to a determination that substantially all of the liquid on the deposition surface plate has evaporated.

3. An apparatus for effecting the controlled evaporation of a solvent from a solution containing a non-volatile solute, said apparatus comprising:
   (a) a deposition surface plate;
   (b) a syringe that is mounted above the deposition surface plate, said syringe including:
      (i) a syringe body for containing a volume of the solution, said syringe body having a plunger end and a needle end;
      (ii) a syringe plunger that is mounted within the syringe body at the plunger end, which plunger is movable within the syringe body so as to dispense a quantity of the solution from the syringe body through the needle end thereof;
      (iii) a needle that is attached to the syringe body at the needle end thereof and in fluid communication therewith, said needle being positioned with respect to the deposition surface plate so that a droplet of the solution that is dispensed from the syringe body through the needle will be deposited onto the deposition surface plate;
      (iv) a collar that is secured around the exterior of the needle in a position above the droplet;
   (c) means for detecting the evaporation of at least a portion of the solvent from a droplet of the solution on the deposition surface plate;
   (d) means for intermittently actuating the plunger so as to deposit a droplet of the solution onto the deposition surface plate;
   (e) means for controlling the actuation of the plunger in response to a determination that at least a portion of the solvent in a droplet of the solution on the deposition surface plate has evaporated;
   (f) means for measuring the solute that remains on the deposition surface plate after substantially all of the solvent in the quantity of the solution has been evaporated.

4. The apparatus of claim 3 which includes a heater that heats the deposition surface plate so as to increase the rate of evaporation of the solvent in a droplet of the solution that has been deposited thereon.

5. The apparatus of claim 3 wherein the means for intermittently actuating the plunger comprises a stepping motor having a spiral shaft with a non-rotating end section attached thereto, said end section being in contact with the plunger, and which stepping motor moves said end section in a series of discrete steps against said plunger.

6. The apparatus of claim 3 wherein the needle has a blunt end and an internal diameter of less than about 0.5 mm.

7. The apparatus of claim 3 wherein the detecting means comprises a weigh cell that is mounted on the deposition surface plate and detects a change in the weight of the droplet on the deposition surface plate as at least a portion of the solvent therein is evaporated.

8. The apparatus of claim 3 wherein the detecting means comprises a piezo-electric crystal that is mounted on the deposition surface plate and means for detecting a change in the deflection of the crystal resulting from the presence of a droplet of the solution on the deposition surface plate as at least a portion of the solvent therein is evaporated.

9. The apparatus of claim 3 wherein the detecting means comprises:
   (a) a source of electromagnetic waves that is arranged so as to transmit a beam of such waves across the deposition surface plate and through a droplet that has been deposited thereon;
   (b) a detector of electromagnetic waves that is arranged so as to detect the beam of such waves emanating from the source;
   (c) means for determining that the beam of waves from the source is at least partially obscured by the presence of the solvent in a droplet of the solution on the deposition surface plate.

10. The apparatus of claim 9 wherein the source of electromagnetic waves is a visible light source, and the detector is a video camera.

11. The apparatus of claim 9 which includes a diffuser of electromagnetic waves that is positioned between the source and the deposition surface plate.

12. The apparatus of claim 9 wherein the source is a laser beam source which is arranged so as to direct a laser beam onto the deposition surface plate so that the beam will strike the deposition surface plate at an acute angle beneath the needle.

13. The apparatus of claim 3 which includes:
   (a) an enclosure that encloses the deposition surface plate, said enclosure having:
      (i) a top access hole through which the needle passes;
      (ii) a seal that seals the top access hole around the needle;

(iii) an inlet for purge gas; and
(iv) an outlet for purge gas;
(b) a purge gas source that is in fluid communication with the purge gas inlet of the enclosure; and
(c) a regulator for regulating the flow of purge gas into the enclosure.

14. The apparatus of claim 13 which includes a gas filter between and in fluid communication with the regulator and the purge gas inlet of the enclosure.

15. The apparatus of claim 13 wherein the detecting means comprises a vapor detector that is located adjacent to the outlet for purge gas, which detector detects solvent vapors emanating from the outlet so as to determine that at least a portion of the solvent in a droplet of the solution on the deposition surface plate has evaporated.

16. A method for effecting the controlled evaporation of a liquid, said method comprising:
(a) placing a quantity of liquid into a depositing device;
(b) depositing a droplet of the liquid onto a deposition surface plate;
(c) evaporating at least a portion of the droplet of the liquid;
(d) determining that at least a portion of the liquid on the deposition surface plate has evaporated;
(e) controlling the depositing device so as to deposit a droplet of the liquid onto the deposition surface plate in response to a determination that at least a portion of the liquid on the deposition surface plate has evaporated; and
(f) repeating steps (c), (d) and (e) until the quantity of liquid in the depositing device has been deposited onto the deposition surface plate.

17. The method of claim 16 which includes heating the deposition surface plate to a suitable temperature and regulating said temperature so as to increase the rate of evaporation of the liquid thereon.

18. A method for effecting the controlled evaporation of a solvent from a solution containing a non-volatile solute, said method comprising:
(a) placing a quantity of solution into a syringe having a plunger which moves within the syringe and a needle through which a droplet of solution may be dispensed;
(b) actuating the plunger so as to dispense a droplet of the solution from the syringe through the needle onto a deposition surface plate, which is located below the syringe needle;
(c) evaporating at least a portion of the droplet of the solution;
(d) determining that at least a portion of the solvent in the droplet of the solution on the deposition surface plate has evaporated;
(e) repeating steps (b), (c) and (d) until the quantity of the solution in the syringe has been dispensed therefrom onto the deposition surface plate; and
(e) measuring the solute that remains on the deposition surface plate after substantially all of the solvent in the quantity of solution has been evaporated.

19. The method of claim 18 which includes heating the deposition surface plate to a suitable temperature and regulating said temperature so as to increase the rate of evaporation of the solvent in a droplet of the solution thereon.

20. The method of claim 18 which includes:
(a) enclosing the deposition surface plate in an enclosure which includes a top access hole through which the syringe needle passes, a seal that seals the top access hole around the needle, an inlet for purge gas and an outlet for purge gas;
(b) introducing a purge gas into the enclosure through the purge gas inlet;
(c) conveying the purge gas out of the enclosure through the purge gas outlet.

* * * * *